United States Patent
Haley

(10) Patent No.: US 8,349,120 B2
(45) Date of Patent: Jan. 8, 2013

(54) MULTI-LAYER PATCH MADE ON A SHEET AND ENCLOSED IN A BLISTER

(75) Inventor: Jeffrey T Haley, Mercer Island, WA (US)

(73) Assignee: Ora Health Corporation, Bellevue, WA (US)

( * ) Notice: Subject to any disclaimer, the term of this patent is extended or adjusted under 35 U.S.C. 154(b) by 880 days.

(21) Appl. No.: 12/231,841

(22) Filed: Sep. 5, 2008

(65) Prior Publication Data

US 2009/0010997 A1 Jan. 8, 2009

Related U.S. Application Data

(63) Continuation of application No. PCT/US2007/005947, filed on Mar. 7, 2007.

(60) Provisional application No. 60/780,009, filed on Mar. 7, 2006, provisional application No. 60/795,637, filed on Apr. 26, 2006.

(51) Int. Cl.
*B32B 37/06* (2006.01)

(52) U.S. Cl. ......................... 156/283; 156/291; 424/447

(58) Field of Classification Search .................. 156/283, 156/291, 282; 424/447

See application file for complete search history.

(56) References Cited

U.S. PATENT DOCUMENTS

| | | | |
|---|---|---|---|
| 3,312,594 A | 4/1967 | Cyr | |
| 3,862,338 A * | 1/1975 | Sapsowitz | ......................... 426/3 |
| 4,292,299 A | 9/1981 | Suzuki | |
| 4,772,470 A | 9/1988 | Inoue | |
| 4,876,092 A | 10/1989 | Mizobuchi | |
| 5,236,713 A | 8/1993 | Wato | |
| 5,330,761 A | 7/1994 | Baichwal | |
| 5,409,703 A | 4/1995 | McAnalley | |
| 5,578,315 A | 11/1996 | Chien | |
| 5,700,478 A | 12/1997 | Biegajski | |
| 5,713,852 A | 2/1998 | Anthony | |
| 5,780,045 A | 7/1998 | McQuinn | |
| 5,800,832 A | 9/1998 | Tapolsky | |
| 5,985,317 A | 11/1999 | Venkateshwaran | |
| 6,159,498 A | 12/2000 | Tapolsky | |
| 6,197,331 B1 | 3/2001 | Lerner | |
| 6,210,699 B1 | 4/2001 | Acharya | |
| 6,251,466 B1 * | 6/2001 | McGuire et al. | .............. 426/577 |
| 6,303,147 B1 | 10/2001 | Gilis | |
| 6,319,510 B1 | 11/2001 | Yates | |
| 6,375,963 B1 | 4/2002 | Repka | |

(Continued)

OTHER PUBLICATIONS

Nagia, Tsuneji and Machida, Yoshiharu; "Mucosal adhesive dosage forms"; published in Pharmacy International, 6(8) Aug. 1985, pp. 196-200.

*Primary Examiner* — Khanh P Nguyen
*Assistant Examiner* — Vishal I Patel

(57) ABSTRACT

A muco-adhesive patch for delivery of drugs into mucous membranes. On the muco-contact side, a water impermeable layer covers the center of the patch and less than half of the muco-contact side of the patch. Drugs may be added by mixing the drug with an adhesive material and placing a spot of the drug plus adhesive onto the exposed side of the water impermeable layer. A lenticular medical patch with a thin, tapered edge can be made with multiple layers by passing a single sheet such as a sheet of plastic through a production line in which each layer is applied in turn maintaining registration by reference to edges of the sheet or to marks on the sheet.

11 Claims, 1 Drawing Sheet

U.S. PATENT DOCUMENTS

| | | |
|---|---|---|
| 6,387,392 B1 | 5/2002 | Saito |
| 6,585,997 B2 | 7/2003 | Moro |
| 7,001,609 B1 | 2/2006 | Matson |
| 2002/0155231 A1* | 10/2002 | Ellson et al. .................. 427/600 |
| 2003/0003140 A1 | 1/2003 | Domb |
| 2004/0142036 A1* | 7/2004 | Abrams et al. ................ 424/473 |

* cited by examiner

MULTI-LAYER PATCH MADE ON A SHEET AND ENCLOSED IN A BLISTER

PRIORITY CLAIM

This application claims priority from PCT/US2007/005947 filed Mar. 7, 2007 (continuation) U.S. patent application 60/780,009 filed Mar. 7, 2006 and from U.S. patent application 60/795,637 filed Apr. 26, 2006, which applications are incorporated herein by reference in their entirety.

BACKGROUND

For conditions that must be treated by delivering drugs through the blood stream, medical science has developed new drugs that cannot be delivered to the blood via the stomach because acids and enzymes of the stomach will destroy them. Examples of such drugs include protein drugs, drugs made with peptide molecular groups, and vaccines. These drugs must be delivered by injection or by absorption through mucous membranes, such as mucous membranes of the mouth, nose, or vagina. For delivery in the mouth, it is known to put such drugs in a dissolving tablet or lozenge or film that is held in the mouth until the delivery vehicle has dissolved. With this delivery method, a large portion of the delivered drug will be swallowed down the throat along with saliva and that portion is wasted. For drugs that are inexpensive and the range of suitable dosage is wide, such as vitamin B12, one can merely provide enough quantity of the drug that the portion absorbed through the mucosal membranes of the mouth provides a sufficient dose. However, for expensive drugs that cannot be delivered through the stomach, the waste increases cost too much for practical use. And this method can not be used where the suitable dosage range requires greater precision because a large portion will go down the throat one time but not another time.

Also, for drugs that should be delivered via a muco-adhesive patch to a single spot in the mouth, the action of the muco-adhesive drawing water from a spot can prevent the drug from diffusing into the spot.

The first muco-adhesive oral patch was made by pressing grains into a thin, wide tablet. The tablet can be made to adhere on only one side by first pressing into a tablet die a small amount of powder and then adding more powder of a different composition and pressing again. Canker Cover, sold by Quantum, is an example. Orajel ("Protective Mouth Sore Discs") improved the shape by making each side domed and making the edge as thin as possible to produce a lenticular shape. However, a thin edge is inconsistent with multiple layers.

Pressing grains into a tablet can never make a patch that is flexible and yet strong enough not to fall apart because there are no fibers or polymer strands that cross grain boundaries. If the grains become elastic enough to flex, due to heat or moisture, the grains will pull apart from each other.

Pressing grains into a tablet also can not produce a thin, tapered edge. There must always be a substantial straight vertical "cliff" edge to the tablet because the machines that make them must have the flexibility to produce a range of thicknesses in each tablet to ensure that adequate pressure is applied. In other words, the thickness of the edge must be determined by achieving the proper pressure, not by the final thickness dimension, which requires that the edge thickness vary according to the exact amount and composition of the powders put into the press for each tablet. The Orajel patch was produced with the thinnest edge practical by tablet pressing, about 0.75 mm, which is about 30 thousandths of an inch. To press a tablet with two layers requires a cliff edge at least twice this thick.

The only solution to the problem of strength with flexibility described above is to mix the preferred ingredients together in a liquid and then cure it to a solid. The mixture will include long polymer molecules, some of which may be organized into fibers. The curing may be accomplished by cooling or by evaporating a solvent or both.

In a prior art method implementing this solution, the preferred ingredients are mixed together and heated to a liquid, then formed to a sheet, and then cooled. Because long chain molecules can be intertwined with no grain boundaries, it is strong yet can be flexible. The sheets can be formed by pouring onto a flat table, like making glass, or can be rolled or extruded. Layers can be separately formed and then bonded together or can be co-extruded. The sheet is then die cut into patches of the preferred shape.

Like the tablet press method, the die-cut sheet method can not produce a thin, tapered edge. The edges of the patch cut by the die are vertical "cliff" edges. Nor can it produce a lenticular shape. Both sides are flat.

SUMMARY OF THE INVENTION

In one aspect, the invention is a muco-adhesive patch for delivery of drugs into mucous membranes wherein muco-adhesive material is formed into a planer base with a non-adhesive layer adhered to a non-muco-contact side of the base and covering the entire non-muco-contact side. On the muco-contact side of the base, a water impermeable layer covers the center of the patch and less than half of the muco-contact side of the patch. Drugs may be added to this patch for delivery into mucous membranes by mixing the drug with an adhesive material (if it is not sufficiently adhesive by itself) and placing a spot of the drug (plus adhesive) onto the exposed side of the water impermeable layer.

A person who wishes to take the drug places the patch in the mouth with the drug against the mucous membrane of the buccal (cheek), with the non-adhesive side of the patch contacting the teeth or gums opposite the buccal. The ring of the muco-contact side of the base that is not covered with a water impermeable layer adheres to the mucous of the buccal and prevents saliva from passing between this portion of the base and the buccal, thereby isolating the drug from saliva flow. Because the drug cannot pass through the water impermeable layer, it can only migrate into the mucous membrane of the buccal.

When a muco-adhesive patch adheres to a mucous membrane, the patch must absorb water from the membrane to prevent a layer of water from accumulating between them and interfering with adhesion. This causes a net flow of water through the surface of the membrane into the patch. This flow significantly impedes migration of molecules in the opposite direction, from the patch into the membrane. The water impermeable layer in the center of the adherent side of the patch blocks flow of water through this area, allowing the drug to migrate into the membrane.

A portion of the drug which enters the mucous membrane will travel laterally in the mucous membrane beyond the edge of the impermeable layer and then either flow into the saliva in the mouth or be absorbed by the non-coated portion of the patch. For this reason, it is preferred to place the drug in a relatively small spot at the center of a relatively larger impermeable layer to minimize the amount of drug that travels through the membrane around the end of the impermeable layer and into the patch or the saliva.

The present method and device are suitable for use with volatile drugs and excipients, as no heat treatment step is involved or necessary. Thus, the present invention is useful with drugs such as nicotine, nitroglycerin, amyl nitrate, and scopolamine. The present device is also useful with drugs such as fentanyl, which will typically be incorporated into the patch using nonaqueous, volatile vehicles and/or enhancers which, because they volatilize during heat treatment, have proven difficult to incorporate into a transdermal delivery device by conventional means.

Since the inherent permeability of the epithelium to some drugs, such as steroids, is too low to permit therapeutic levels of such drugs to pass through a reasonably sized area of unbroken skin, it is necessary to coadminister a percutaneous absorption enhancer with such drugs. Accordingly, in such a case, a percutaneous absorption enhancer will be present in the device along with the drug, i.e., will be initially deposited on the impermeable layer together with the drug. Any of the many percutaneous absorption enhancers known in the art may be used in conjunction with the present invention. For examples of suitable enhancers, see U.S. Pat. Nos. 3,996,934; 4,460,372; 4,552,872; 4,557,934 and 4,568,343, which are hereby incorporated by reference, and the patents referenced therein.

The best shape for a medical patch is lenticular with a thin, tapered edge. If the edge has vertical sides of any significant dimension, it will catch on the tongue and teeth and tend to dislodge the patch. It will also feel unattractive to the user. It is best if the patch is thickest at the center and tapers toward the edges. Then, as the patch erodes, it will tend to hold together, getting thinner and smaller, rather than breaking into pieces. Such a medical patch can be made with multiple layers by passing a single sheet such as a sheet of plastic through a production line in which each layer is applied in turn maintaining registration by reference to edges of the sheet or to marks on the sheet. Each layer as applied need be no larger than necessary so no trimming is required, and the sheet can be used as packaging material.

DETAILED DESCRIPTION

Figure 1:
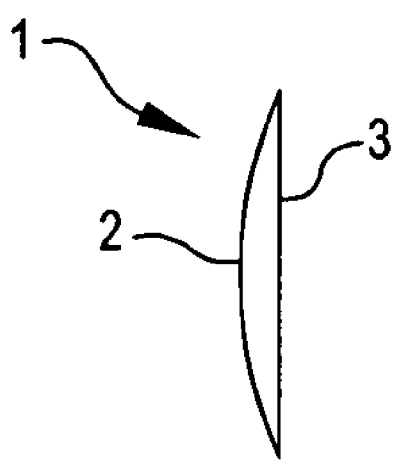
FIG. 1 shows a side view of a patch made according to the present invention.

FIG. 1 shows, in side view, an embodiment of the patch 1 comprising a planer base having a muco-contact side 3 and a non-muco-contact side 2. The non-muco-contact side 2 is entirely covered with a layer that presents it from being adhesive to any of mucous membranes, gums, teeth, or orthodontic devices, such as any hydrophobic material such as a lipid.

Figure 2:
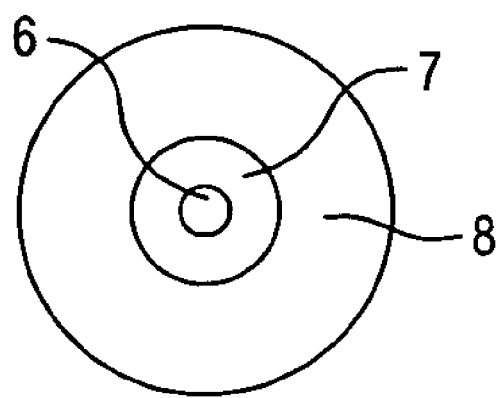
FIG. 2 shows the muco-contact side of a patch made according to the present invention.

FIG. 2 shows the muco-contact side of the patch. An outer ring 8 of the muco-contact side is not covered with an impermeable membrane, leaving exposed the muco-adhesive material of the patch. A central portion of the muco-contact side is covered with an impermeable layer 7 which blocks passage of water and large molecules, including drug molecules. Drug molecules (plus binder molecules if needed) are adhered in a spot 6 in the center of the impermeable layer 7 on the muco-contact side of the patch.

The planer base may be made by extruding planar material and then cutting to a desired shape or by pressing powders into a tablet of the desired shape or by depositing a blob of viscous liquid and then curing the deposited blob to a solid.

One way of making the patch is taught in U.S. patent application Ser. No. 11/157,054 which is incorporated by reference.

One method for coating a side of the patch to make it non-adhesive is to spray on a layer of liquid hydroxy-propyl-ethyl-cellulose (HPEC) or hydroxy-propyl-methyl-cellulose (HPMC) or shellac, and then evaporating away a solvent which carries the liquid coating material. Examples of suitable GRAS-certified materials include but are not limited to monoglycerides, triglycerides, waxes such as paraffin, fatty acids, fatty alcohols and mixtures thereof. Sorbitan monostearate (SPAN 60) with hydroxypropyl cellulose (HPC LF) is suitable If the base is made by pressing powders in a tablet press, a non-adhesive layer may be made by prior art techniques for making a two layer tablet. First, a thin tablet is made by pressing powders into a female die and lower with a male upper punch, then the male punch is removed, additional powders are added for the second layer, and the male punch is inserted once again. Either layer can be formed first. An oral patch called Canker Cover sold by Quantum, Inc. of Eugene Oreg. is made by this method.

If the base is made by extrusion, the non-adhesive layer can be extruded onto the base or co-extruded along with the base. A patch made this way called BEMA is marketed by Bio Delivery Sciences International of Texas.

The spot of impermeable material can be added to the base by any printing method such as silk screen printing, Gravure-type printing, or extrusion coating. Once the impermeable layer has cured, a smaller spot of drug plus adhesive molecules can be added, again by any printing process such as silk screen printing.

When the base is made by depositing a blob of viscous liquid and then curing to a solid, the preferred method implements the following steps. First, a small spot of drug plus adhesive is printed in many spots on a sheet of plastic. Then, when this is sufficiently cured, such as by evaporation or gelation, the impermeable layer is printed on top of these spots. Then, when this layer is sufficiently cured, such as by evaporation or gelation, the viscous liquid is deposited onto each of the spots. Then, when the viscous liquid is cured, such as by evaporation or gelation or both, a non-adhesive coating is sprayed onto each base and the coating is cured. At this point, the patches are still adhered to the original layer of plastic. They are then encased with a layer of film, such as aluminum foil, that is sealed to the plastic around the circumference of each patch and the entire assemblage is die cut to a final product.

A suitable binder for holding the drug to the plastic is HPMC, which is water soluble. Suitable materials for the impermeable layer are HPEC or shellac, which are not water soluble.

Suitable materials for the base include the hydrophilic gums, the more hydrophilic the better for maintaining adhesion until the drug has been fully absorbed into the mucous membrane. These materials include xanthan gum, konjac gum, guar gum, carrageen, agar, gelatin, pectin, cellulose, starch, maltodextrin or other polysaccharides, diblock copolypeptide amphiphiles, carboxymethylcellulose, hydroxymethylcellulose, polyacrylic acid, and carbopol-934. To maintain flexibility, a plasticizer, such as glycerol, may be included.

Suitable material for the non-adhesive layer is HPEC or shellac with a plasticizer to make it flexible enough to avoid cracking as the patch flexes.

Patch with Thin, Tapered Edge

There are three methods for making an oral patch with a thin, tapered edge. The first method is to mix the preferred ingredients into a liquid with a solvent, deposit blobs of the liquid onto a sheet or into shallow, dished molds, and then dry out the solvent, causing the blobs to thin into the perfect shape, thickest at the center and tapering to a thin edge. This is the method by which Oramelts Corporation manufactures Cankermelts. This method is highly economical because the sheet is used as a part of the final packaging and, after drying, a foil lid is heat sealed over the patches. Use of the solvent requires only modest temperatures that present no complications for manufacturing, and water can be used as the solvent to minimize cost and problems for workers. Once the patch material is dropped out of the depositor machine, it never touches any surface except the final packaging materials, minimizing contamination risk.

The second method is to liquify the preferred ingredients with heat, inject the liquid into molds, and then cure by cooling. This is the same process as for making injection molded thermoplastic parts. A plastic sheet liner can be put into one side of the mold so that the patch remains adhered to the liner when it is demolded. The plastic sheet then becomes a part of the final packaging.

The third method is to start with a sheet, like the prior art die-cut method, and then apply a hot press that melts and deforms the sheet material to produce a thin, tapered edge and a raised center. By this method, all the material in a sheet can be forced into the body of one of the patches, which may be close-packed rectangles with rounded corners or hexagonally-close-packed circles, leaving no waste trimmings between patches. The heat and pressure can be applied through a layer of flexible packaging material on each side of the patch so that the patches need not touch the hot press surfaces to minimize contamination risk.

Multi-Layers

For various purposes, it is desirable to add a thin layer of different material on one side of the patch or the other, such as to block drug release or eliminate adhesiveness or stop water migration on one side or provide a burst drug release on one side. This can be done by three methods.

1. Spraying: Spraying a coating on one side of the patch or spraying a spot of coating on the plastic sheet before the patch body is deposited allows a coating to be placed on either side of the patch. A small nozzle sprays a circle of preferred diameter at the right spot. These methods work better than spraying on tablets or extruded sheets of patch material because the plastic sheet maintains registration for all steps in the process and no sprayed material is wasted by over spray or by spraying base material that is trimmed off.

2. Depositing: Granular materials that can not be sprayed can be suspended in a high viscosity gel, such as benzocaine crystals suspended in xanthan gum in water, and deposited as a blob of preferred diameter on the plastic sheet. The blob is then dried before the patch body is deposited. Because the blob is mostly water, it will dry to a thin layer. Like with spraying, the plastic sheet maintains the registration.

3. Printing: To place a spot of material on one side of the patch with a sharply defined edge, printing heads can be placed over the production line on which the plastic sheet moves. The head openings can be selected to deposit a liquid in a layer of uniform thickness of a preferred diameter at the preferred spot on the plastic sheet, either as a first layer or as a second layer on top of a previously sprayed or printed layer. The preferred printing method is screen printing, but flexo and gravure printing can also be used.

Although the present invention has been described in detail with reference to certain preferred embodiments, other embodiments are possible. Therefore, the spirit or scope of the appended claims should not be limited to the description of the embodiments contained herein. It is intended that the invention resides in the claims hereinafter appended.

What is claimed is:

1. A method of making a multi-layer patch with registration of multiple layers enclosed in a blister of sheet and film, comprising:
   a. placing molecules of a drug into a plurality of locations on a sheet to form a plurality of drug spots each separated from the other by at least one space of uncovered sheet;
   b. placing molecules of a base material in contact with each drug spot and entirely covering each drug spot to form a plurality of base spots each separated from the other by at least one space of uncovered sheet;
   c. molecules of a second layer in contact with each base placing spot and covering substantially all of each base spot to make a multi-layer spot;
   d. heat sealing a layer of film to the sheet covering the plurality of multi-layer spots to make a sandwich of sheet and film with the film heat sealed to the sheet in the uncovered spaces between multi-layer spots and enclosing each multi-layer spot in a blister of sheet and film containing only one multi-layer spot; and
   e. cutting the sandwich to form a plurality of cards, each card containing one or more blisters, each blister containing one multi-layer spot.

2. The method of claim 1 wherein the base material is deposited as a viscous liquid.

3. The method of claim 1 wherein the second layer is sprayed on the base material.

4. The method of claim 1 further comprising, after the drug spot is placed and before the base layer is placed, placing molecules of a substantially water impermeable layer on top of each drug spot and entirely covering each drug spot.

5. The method of claim 4 wherein the substantially water impermeable layer is printed onto the sheet and drug spots.

6. The method of claim 1 wherein the sheet comprises thermoplastic material.

7. The method of claim 1 wherein the base material is printed.

8. The method of claim 1 wherein the base material is made by pressing powder into a tablet.

9. The method of claim 1 wherein the second layer is made by pressing powders into a tablet.

10. The method of claim 1 wherein the drug spots are printed onto the sheet.

11. The method of claim 1 wherein the film is aluminum foil.

* * * * *